United States Patent [19]

Boireau et al.

[11] Patent Number: 5,658,900
[45] Date of Patent: Aug. 19, 1997

[54] APPLICATION OF CARBAMAZEPINE AND OXCARBAZEPINE IN THE TREATMENT OF PARKINSON'S DISEASE AND PARKINSONIAN SYNDROMES

[75] Inventors: Alain Boireau, Sucy En Brie; Françoise Bordier; Adam Doble, both of Paris; Pierre Dubedat, Nogent sur Marne; Erik Louvel, Paris; Mireille Meunier, Dourdan; Jean-Marie Miquet, Orsay; Jean-Marie Stutzmann, Villecresnes, all of France

[73] Assignee: Rhone-Poulenc Rorer S.A., Antony, France

[21] Appl. No.: 446,735

[22] PCT Filed: Jan. 3, 1994

[86] PCT No.: PCT/FR94/00004

§ 371 Date: Jun. 6, 1995

§ 102(e) Date: Jun. 6, 1995

[87] PCT Pub. No.: WO94/15610

PCT Pub. Date: Jul. 2, 1994

[30] Foreign Application Priority Data

Jan. 7, 1993 [FR] France ................................. 93 00074

[51] Int. Cl.⁶ ............................................. A61K 9/24
[52] U.S. Cl. ................................................. 514/217
[58] Field of Search .................................... 514/217

[56] References Cited

U.S. PATENT DOCUMENTS

| 2,948,718 | 8/1960 | Schindler et al. | 260/239 |
|---|---|---|---|
| 3,642,775 | 2/1972 | Schindler et al. | 260/239 |
| 4,431,641 | 2/1984 | Mondadori . | |

FOREIGN PATENT DOCUMENTS

| 0 050 589 | 4/1982 | European Pat. Off. . |
|---|---|---|
| 0 517 347 | 12/1992 | European Pat. Off. . |

OTHER PUBLICATIONS

Neuroreport, vol. 1, No. 1, 1990 pp. 26–28, H. Lampe et al., "Carbamazepine Blocks NMDA–Activated Currents in Cultured Spinal ... ".

Experientia, vol. 48, No. 8, 1992, pp. 751–753, J.M. Lancaster et al., "Carbamazepine Inhibits NMDA–Induced Depolarizations in Cortical ... ".

Soc. Neurosci. Abstr., vol. 18, No. 1–2, 1992, pp. 381, T. Dalkara et al., "Carbamazepine and Phenytoin Inhibit NMDA Receptor–Mediated ... ".

Trends in Neurosciences, vol. 12, No. 8, 1989, pp. 285–286, Klockgether "Excitatory Amino Acids and the Basal Ganglia: Implications for ... ".

Neurology, vol. 37, No. SUPL. 1987, p.339, E. Melamed et al., "Effect of Anticonvulsants on the Neurotoxicity of MPTP ... ".

J.E.F. Reynolds, "Martindale, The Extra Pharmacopoeia", 1989, The Pharmaceutical Press, London pp. 400–402.

Embase Abstract # 92250451, Cai et al, Eur. J. Pharmacol. (1992) 219/1 (53–57). Abstract only.

Life Sciences, vol. 54, No. 4, 1994, pp. 245–252, Stacey et al., "The Novel Anticonvulsant Lamotrigine Prevents Dopamine Depletion ... ".

Chemical Abstracts, vol. 115, No. 15, Oct. 1991, Ohio, abstract No. 150162.

*Primary Examiner*—Keith MacMillan
*Attorney, Agent, or Firm*—Finnegan, Henderson, Farabow, Garrett & Dunner, L.L.P.

[57] ABSTRACT

This invention relates to an application of an anticonvulsant selected from carbamazepine and oxcarbazepine or the pharmaceutically acceptable salts of said compounds in the preparation of drugs for the treatment of Parkinson's disease and parkinsonian syndromes.

2 Claims, No Drawings

APPLICATION OF CARBAMAZEPINE AND OXCARBAZEPINE IN THE TREATMENT OF PARKINSON'S DISEASE AND PARKINSONIAN SYNDROMES

FIELD OF THE INVENTION

The present invention relates to a novel therapeutic application of anticonvulsants chosen from carbamazepine and oxcarbazepine or the pharmaceutically acceptable salts of these compounds.

BACKGROUND OF THE INVENTION

Carbamazepine and oxcarbazepine are described as anticonvulsants and antiepileptics, in particular in Patent EP 50,589.

DESCRIPTION OF THE INVENTION

It has now been found, surprisingly, that these compounds may also be used in the treatment of Parkinson's disease and parkinsonian syndromes.

The neurotoxin MPTP (1-methyl-4-phenyl-1,2,3,6-tetrahydropyridine) is known to induce a syndrome similar to Parkinson's disease. This syndrome results from a degeneration of the dopaminergic nigrostriatal neurons in primates (R. S. Burns et al., Proc. Natl. Acad. Sci., 80, 4546–4550 (1983)), in man (J. W. Langston et al., Science, 219, 979–980 (1983)) and in mice (R. E. Heikkila et al., Science, 224, 1451–1453 (1984)).

EXAMPLES

The activity of the products was hence demonstrated in mice by measuring MPTP-induced decreases in the levels of striatal dopamine, of 3,4-dihydroxyphenylacetic acid and of homovanillic acid in comparison with those of control animals.

Mice (C57BL/6) weighing 20–25 g are injected intraperitoneally 3 times at 2-hour intervals with 15 mg/kg of MPTP. Thirty minutes before the first injection of MPTP, and then 2 hours 30 minutes, 5 hours 30 minutes and 7 hours 30 minutes after the first injection of MPTP, from 1 to 40 mg/kg of the product under study, depending on the product, are administered. Over the next 3 days, from 1 to 40 mg/kg of the product under study, depending on the product, are administered twice daily. The mice are sacrificed 8 days after injection of MPTP. The striatum is dissected and stored at −70° C. until the time of its analysis. Dopamine, 3,4-dihydroxyphenylacetic acid and homovanillic acid levels are measured by high pressure liquid chromatography with electrochemical detection. Statistical analyses are performed using ANOVA followed by Scheffé's test.

The results obtained with doses of 20 mg/kg of carbamazepine are recorded in the following table:

|  | 3,4-dihydroxyphenylacetic acid level pmol/mg in the striatum (% relative to controls) | homovanillic acid level pmol/mg in the striatum (% relative to controls) | dopamine level pmol/mg in the striatum (% relative to controls) |
| --- | --- | --- | --- |
| controls | 54 ± 3 | 95 ± 3 | 856 ± 27 |
| animals receiving only | 22 ± 4 (−59%) | 62 ± 3 (−35%) | 415 ± 22 (−52%) |

-continued

|  | 3,4-dihydroxyphenylacetic acid level pmol/mg in the striatum (% relative to controls) | homovanillic acid level pmol/mg in the striatum (% relative to controls) | dopamine level pmol/mg in the striatum (% relative to controls) |
| --- | --- | --- | --- |
| MPTP animals treated with carbamazepine | 48 ± 4 (−12%) | 90 ± 6 (−5%) | 765 ± 30 (−11%) |

These results demonstrate clearly that these products are capable of preventing MPTP-induced decreases in the dopemine, 3,4-dihydroxyphenylacetic acid and homovanillic acid levels in the stiatum.

As pharmaceutically acceptable salts, the addition salts with inorganic acids, such as hydrochloride, sulphate, nitrate or phosphate, or organic acids, such as acetate, propionate, succinate, oxalate, benzoate, fumarate, maleate, methanesulphonate, isethionate, theophyllineacetate, salicylate, phenolphthalinate or methylenebis(β-hydroxynaphthoate), or substitution derivatives of these derivatives, may be mentioned in particular.

The medicinal products consist of at least one anticonvulsant chosen from carbamazepine and oxcarbazepine, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragées) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporation of sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 400 mg per day via the oral route for an adult, with single doses ranging from 25 to 200 mg of active substance.

Generally speaking, the doctor will determine the appropriate dosage in accordance with the age, the weight and all other factors specific to the subject to be treated.

The examples which follow illustrate medicinal products according to the invention:

EXAMPLE A

Tablets containing a 50 mg dose of active product and having the following composition are prepared according to the usual technique:

| | |
|---|---|
| Active product | 50 mg |
| Mannitol | 64 mg |
| Microcrystalline cellulose | 50 mg |
| Povidone excipient | 12 mg |
| Sodium carboxymethylstarch | 16 mg |
| Talc | 4 mg |
| Magnesium stearate | 2 mg |
| Colloidal silica, anhydrous | 2 mg |
| Mixture of methylhydroxypropyl-cellulose, polyethylene glycol 6000 and titanium dioxide (72:3.5:24.5) q.s. 1 finished film-coated tablet weighing | 245 mg |

EXAMPLE B

Hard gelatin capsules containing a 50 mg dose of active product and having the following composition are prepared according to the usual technique:

| | |
|---|---|
| Active product | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injection containing 10 mg of active product and having the following composition is prepared:

| | |
|---|---|
| Active product | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water | q.s. 4 cm$^3$ |

The invention also relates to the process for preparing medicinal products which can be used in the treatment of Parkinson's disease and parkinsonian syndromes, consisting in mixing an anticonvulsant chosen from carbamazepine and oxcarbazepine or the pharmaceutically acceptable salts of these compounds with one or more compatible and pharmaceutically acceptable diluents and/or adjuvants.

The invention also relates to a method for treating a mammal, and in particular man, having Parkinson's disease or parkinsonian syndromes, comprising the administration of an effective amount of carbamazepine or oxcarbazepine or the pharmaceutically acceptable salts of these compound.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method for treating Parkinson's disease and/or a parkinsonian syndrome, which comprises administering to a patient in need of said treatment an effective amount of a compound selected from carbamazepine, oxcarbazepine and the pharmaceutically acceptable salts thereof.

2. The method according to claim 1, wherein from 25 to 200 mg of carbamazepine or oxcarbazepine are administered to said patient.

* * * * *